(12) United States Patent
Polla

(10) Patent No.: US 7,375,121 B2
(45) Date of Patent: May 20, 2008

(54) CHEMICAL COMPOUNDS

(75) Inventor: Magnus Polla, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 332 days.

(21) Appl. No.: 10/489,530

(22) PCT Filed: Sep. 23, 2002

(86) PCT No.: PCT/SE02/01737

§ 371 (c)(1),
(2), (4) Date: Mar. 12, 2004

(87) PCT Pub. No.: WO03/027128

PCT Pub. Date: Apr. 3, 2003

(65) Prior Publication Data

US 2004/0248852 A1 Dec. 9, 2004

(30) Foreign Application Priority Data

Sep. 28, 2001 (SE) .................................. 0103272

(51) Int. Cl.
*A61K 31/44* (2006.01)
*C07D 211/72* (2006.01)

(52) U.S. Cl. ..................... 514/352; 546/304; 546/339; 546/340

(58) Field of Classification Search ................ 546/304, 546/339, 340; 514/352
See application file for complete search history.

(56) References Cited

U.S. PATENT DOCUMENTS 6,046,180 A 4/2000 Jackson et al.

FOREIGN PATENT DOCUMENTS

| JP | 01/19836 A1 | 3/2001 |
|---|---|---|
| WO | WO-00/66152 A1 | 11/2000 |
| WO | WO-00/66550 A1 | 11/2000 |
| WO | WO-00/66557 A1 | 11/2000 |
| WO | WO-02/14285 A1 | 2/2002 |

OTHER PUBLICATIONS

Cross et al., 1983, CAS: 98: 198019.*
Wang, W., et al., "Carboxypeptidase U, a Plasma Carboxypeptidase with High Affinity for Plasminogen," J. of Biol. Chem., 269(22), 15937-15944 (1994).
Hendriks, D., et al., "Purification and characterization of new arginine carboxypeptidase in human serum," Biochimica et Biophysica Acta, 1034, 86-92 (1990).
Eaton, D., et al., "Isolation, Molecular Cloning, and Partial Characterization of a Novel Carboxypeptidase B from Human Plasma," J. of Bio. Chem., 266(32), 21833-21838 (1991).
Hendriks, D., et al., "Asay of Carboxypeptidase N Activity in Serum by Liquid-Chromatographic Determination of Hippuric Acid," Clin. Chem. 31/12, 1936-1939 (1985).

* cited by examiner

*Primary Examiner*—Rei-tsang Shiao
(74) *Attorney, Agent, or Firm*—Morgan, Lewis & Bockius LLP

(57) ABSTRACT

The present invention concerns compounds of formula (I), and pharmaceutically acceptable salts or solvates thereof, or solvates of such salts,

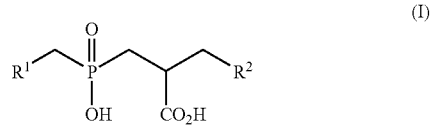

(I)

which compounds inhibit carboxypeptidase U and thus can be used in the prevention and treatment of diseases where inhibition of carboxypeptidase U is beneficial. In further aspects, the invention relates to compounds of the invention for use in therapy; to processes for preparation of such new compounds; to pharmaceutical compositions containing at least one compound of the invention, or a pharmaceutically acceptable salt or solvate thereof, as active ingredient; and to the use of the active compounds in the manufacture of medicaments for the medical use indicated above.

5 Claims, No Drawings

CHEMICAL COMPOUNDS

This application is a national stage filing under 35 U.S.C. 371 of International Application No. PCT/SE02/01737, filed Sep. 23, 2002, which claims priority from United Kingdom Patent Application No. 0103272, filed Sep. 28, 2001, the specification of which are incorporated by reference herein. International Application No. PCT/SE02/01737 was published under PCT Article 21(2) in English.

The present invention relates to novel compounds, and pharmaceutically acceptable salts thereof, which inhibit basic carboxypeptidases, more specifically carboxypeptidase U, and thus can be used in the prevention and treatment of diseases wherein inhibition of carboxypeptidase U is beneficial, such as thrombosis and hypercoagulability in blood and tissue. In further aspects, the invention relates to compounds of the invention for use in therapy; to processes for preparation of such new compounds; to pharmaceutical compositions containing at least one compound of the invention, or a pharmaceutically acceptable salt thereof, as active ingredient; and to the use of the active compounds in the manufacture of medicaments for the medical use indicated above.

Fibrinolysis is the result of a series of enzymatic reactions resulting in the degradation of fibrin by plasmin. The activation of plasminogen is the central process in fibrinolysis. The cleavage of plasminogen to produce plasmin is accomplished by the plasminogen activators, tissue-type plasminogen activator (t-Pa) or urokinase-type plasminogen activator (u-PA). Initial plasmin degradation of fibrin generates carboxy-terminal lysine residues that serve as high affinity binding sites for plasminogen. Since plasminogen bound to fibrin is much more readily activated to plasmin than free plasminogen this mechanism provides a positive feedback regulation of fibrinolysis.

One of the endogenous inhibitors to fibrinolysis is carboxypeptidase U (CPU). CPU is also known as plasma carboxypeptidase B, active thrombin activatable fibrinolysis inhibitor (TAFIa), carboxypeptidase R and inducible carboxypeptidase activity. CPU is formed during coagulation and fibrinolysis from its precursor proCPU by the action of proteolytic enzymes, such as thrombin, thrombin-thrombomodulin complex or plasmin. CPU cleaves basic amino acids at the carboxy-terminal of fibrin fragments. The loss of carboxy-terminal lysines and thereby of lysine binding sites for plasminogen then serves to inhibit fibrinolysis. By inhibiting the loss of lysine binding sites for plasminogen and thus increase the rate of plasmin formation, effective inhibitors of carboxypeptidase U are expected to facilitate fibrinolysis.

2-Mercaptomethyl-3-guanidinoethylthiopropanoic acid is reported as a carboxypeptidase N inhibitor. More recently, this compound has been shown to inhibit CPU, Hendriks, D. et al., Biochimica et Biophysica Acta, 1034 (1990) 86-92.

Guanidinoethylmercaptosuccinic acid is reported as a carboxypeptidase N inhibitor. More recently, this compound has been shown to inhibit CPU, Eaton, D. L., et al., The Journal of Biological Chemistry, 266 (1991) 21833-21838.

CPU inhibitors are disclosed in WO 00/66550 and WO 00/66557, and a pharmaceutical formulation containing a CPU inhibitor and a thrombin inhibitor is disclosed in WO 00/66152.

Inhibitors of plasma carboxypeptidase B are disclosed in WO 01/19836.

Inhibitors of TAFIa are disclosed in WO 02/14285.

It has now been found that compounds of formula (I) are particularly effective as inhibitors of carboxypeptidase U and are thereby useful as medicaments for the treatment or prophylaxis of conditions wherein inhibition of carboxypeptidase U is beneficial.

Thus, the present invention provides a compound of formula (I):

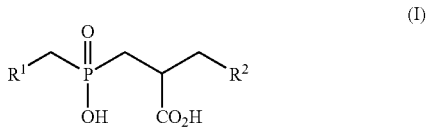

wherein:

$R^1$ is phenyl {optionally substituted by halogen, nitro, cyano, hydroxy, $C_{1-6}$ alkyl (itself optionally substituted by halogen, hydroxy or $S(O)_2R^3$), $C_{1-6}$ alkoxy (itself optionally substituted by halogen), $C_{1-6}$ alkylthio (itself optionally substituted by halogen), phenyl, phenylcarbonyl, phenyloxy, heteroaryl, $S(O)_2R^4$ or $S(O)_2NHR^5$; wherein the foregoing phenyl and heteroaryl rings are optionally substituted by halogen, hydroxy, $C_{1-6}$ alkyl (itself optionally substituted by halogen) or $C_{1-6}$ alkoxy (itself optionally substituted by halogen)}, 9,10-dihydroanthracenyl {optionally substituted by oxo}, naphthyl {optionally substituted by halogen, $C_{1-6}$ alkyl (itself optionally substituted by halogen) or $C_{1-6}$ alkoxy (itself optionally substituted by halogen)}, or heteroaryl {optionally substituted by halogen, $C_{1-6}$ alkyl (itself optionally substituted by halogen), $C_{1-6}$ alkoxy (itself optionally substituted by halogen) or phenylcarbonyl (itself optionally substituted by halogen)};

$R^2$ is aminopyridinyl, aminothiazolyl or 3-azabicyclo[3.2.1]octyl;

$R^3$ is $C_{1-6}$ alkyl or phenyl;

$R^4$ is $C_{1-6}$ alkyl;

$R^5$ is $(CH_2)_2R^6$; and, $R^6$ is phenyl or heteroaryl either of which is optionally substituted by halogen, $C_{1-6}$ alkyl (itself optionally substituted by halogen) or $C_{1-6}$ alkoxy (itself optionally substituted by halogen);

or a pharmaceutically acceptable salt or solvate thereof, or a solvate of such a salt.

The compounds of formula (I) exist in isomeric forms and the present invention covers all such forms and mixtures thereof in all proportions.

The term $C_{1-6}$ alkyl denotes a straight or branched alkyl group having 1 to 6 carbon atoms in the chain. Examples of alkyl include methyl, ethyl, n-propyl, iso-propyl, n-butyl, iso-butyl, sec-butyl and tert-butyl.

The terms $C_{1-6}$ alkoxy and $C_{1-6}$ alkylthio denote, respectively, an alkyl-O-group or an alkyl-S-group, where alkyl is straight or branched chain and as exemplified above.

Heteroaryl is aromatic and includes 4- to 10-membered monocyclic or multicyclic ring systems in which one or more of the atoms in the ring or rings are nitrogen, oxygen or sulfur. Examples include furan, thiophene, pyrrole, oxazole, thiazole, imidazole, pyrazole, isoxazole, isothiazole, oxadiazole, furazan, triazole, 1,2,3-thiadiazole, 1,2,4-thiadiazole, pyridine, pyridazine, pyrimidine, pyrazine, indole, benzo[b]furan, benzo[b]thiophen, quinoline and isoquinoline.

Halogen includes fluoro, chloro, bromo and iodo.

In one particular aspect the present invention provides a compound of formula (I) wherein $R^1$ is phenyl {optionally substituted by halogen, nitro, cyano, hydroxy, $C_{1-6}$ alkyl (itself optionally substituted by halogen, hydroxy or $S(O)_2R^3$), $C_{1-6}$ alkoxy (itself optionally substituted by halogen), $C_{1-6}$ alkylthio (itself optionally substituted by halogen), phenyl, phenylcarbonyl, phenyloxy, heteroaryl (such as 1,2,3-thiadiazolyl), $S(O)_2R^4$ or $S(O)_2NHR^5$; wherein the foregoing phenyl and heteroaryl rings are optionally substituted by halogen, hydroxy, $C_{1-6}$ alkyl (itself optionally substituted by halogen) or $C_{1-6}$ alkoxy (itself optionally substituted by halogen)}; $R^3$ is $C_{1-6}$ alkyl or phenyl; $R^4$ is $C_{1-6}$ alkyl; $R^5$ is $(CH_2)_2R^6$; and, $R^6$ is phenyl or heteroaryl either of which is optionally substituted by halogen, $C_{1-6}$ alkyl (itself optionally substituted by halogen) or $C_{1-6}$ alkoxy (itself optionally substituted by halogen).

When $R^1$ is optionally substituted heteroaryl it is especially pyridine, quinoline, benzo[b]furan or benzo[b]thiophen.

In another aspect the present invention provides a compound of formula (I) wherein $R^1$ is phenyl {optionally substituted by halogen (especially bromo, chloro or fluoro), nitro, cyano, $CF_3$ or $OCF_3$}.

Aminopyridinyl is, for example, 6-aminopyridin-3-yl. Aminothiazolyl is, for example, 2-aminothiazol-5-yl. 3-Azabicyclo[3.2.1]octyl is, for example, 3-azabicyclo [3.2.1]oct-8-yl.

In a further aspect the present invention provides a compound of formula (I) wherein $R^2$ is aminopyridine (for example 6-aminopyridin-3-yl).

The compounds of the present invention can be prepared by adaptation of methods described in the literature, or by using or adapting the Methods presented in the Examples.

For example a compound of formula (I) can be prepared by reacting a compound of formula (II):

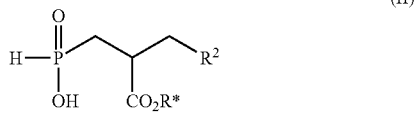

(II)

wherein R* is $C_{1-6}$ alkyl and the amino group in $R^2$ being protected with a tert-butoxycarbonyl moiety, with a suitable halide of formula $R^1CH_2$halide, either:

in the presence of a suitable catalyst (such as bis(trimethylsilyl)trifluoroacetamide (BSTFA)) in a suitable solvent at an elevated temperature (such as in the range 30-50° C.); or, in the presence of a suitable catalyst (such as BSTFA) in a suitable solvent at an elevated temperature (such as in the range 120-160° C.); wherein the heating is achieved using microwave power of appropriate frequency;

and subsequently hydrolysing the ester group and deprotecting the amino group of $R^2$.

It will be appreciated that in the process described above other functional groups of intermediate compounds may need to be protected by protecting groups.

Functional groups which it is desirable to protect include hydroxy, carboxylate and phosphinate groups. Suitable protecting groups for hydroxy include trialkylsilyl or diarylalkyl-silyl (for example tert-butyldimethylsilyl, tert-butyldiphenylsilyl or trimethylsilyl), tetrahydropyranyl and benzyl. Suitable protecting groups for carboxylate and phosphinate include ethyl, tert-butyl and benzyl esters. The use of protecting groups is described in 'Protective Groups in Organic Synthesis', 2nd edition, T. W. Greene & P. G. M. Wutz, Wiley-Interscience (1991). The protective group may also be a polymer resin such as Wang resin or a 2-chorotrityl chloride resin.

The compounds of the invention are inhibitors of carboxypeptidase U and are thus expected to be useful in those conditions where inhibition of carboxypeptidase U is beneficial, such as in the treatment or prophylaxis of thrombosis and hypercoagulability in blood and tissues of mammals, such as man.

It is known that hypercoagulability may lead to thromboembolic diseases. Conditions associated with hypercoagulability and thrombo-embolic diseases which may be mentioned include protein C resistance and inherited or acquired deficiencies in antithrombin III, protein C, protein S and heparin cofactor II. Other conditions known to be associated with hypercoagulability and thrombo-embolic disease include circulatory and septic shock, circulating antiphospholipid antibodies, homocysteinemia, heparin induced thrombocytopenia and defects in fibrinolysis. The compounds of the invention are thus indicated both in the therapeutic and/or prophylactic treatment of these conditions. The compounds of the invention are further indicated in the treatment of conditions where there is an undesirable excess of proCPU/CPU.

Particular disease states which may be mentioned include the therapeutic and/or prophylactic treatment of venous thrombosis and pulmonary embolism, arterial thrombosis (for example in myocardial infarction, unstable angina, thrombosis-based stroke and peripheral arterial thrombosis) and systemic embolism usually from the atrium during atrial fibrillation or from the left ventricle after transmural myocardial infarction.

Moreover, the compounds of the invention are expected to have utility in prophylaxis of re-occlusion and restenosis (that is, thrombosis) after thrombolysis, percutaneous transluminal intervention (PTI) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism, fibrinolytic treatment when blood is in contact with foreign surfaces in the body, such as vascular grafts, vascular stents, vascular catheters, mechanical and biological prosthetic valves or any other medical device, and fibrinolytic treatment when blood is in contact with medical devices outside the body, such as during cardiovascular surgery using a heart-lung machine or in haemodialysis.

Furthermore, the compounds of the invention are expected to have utility in prophylaxis of atherosclerotic progression and transplant rejection in patients subject to organ transplantation, especially renal transplantation.

The compounds of the invention may also be combined and/or co-administered with any antithrombotic agent with a different mechanism of action, such as an anticoagulant (for example a vitamin K antagonist, an unfractionated or low molecular weight heparin, a synthetic heparin fragment such as fondaparinux, a thrombin inhibitor, a factor Xa inhibitor or other coagulation factor/enzyme inhibitor, a recombinant coagulation factor such as a recombinant human activated protein C) or an antiplatelet agent (such as acetylsalicylic acid, dipyridamole, ticlopidine, clopidogrel or other ADP-receptor [such as a P2Y12 or P2Y1] antagonist, a thromboxane receptor and/or synthetase inhibitor, a fibrinogen receptor antagonist, a prostacyclin mimetic or a phosphodiesterase inhibitor).

The compounds of the invention may further be combined and/or coadministered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction, ischaemic stroke and massive pulmonary embolism.

The inhibiting effect of the compounds of the present invention was estimated using the assay described in: Dirk Hendriks, Simon Scharpé and Marc van Sande, Clinical Chemistry, 31, 1936-1939 (1985); and Wei Wang, Dirk F. Hendriks, Simon S. Scharpé, The Journal of Biological Chemistry, 269, 15937-15944 (1994).

Thus, the present invention provides a compound of formula (I), or a pharmaceutically acceptable salt or solvate thereof, or a solvate of such a salt, as hereinbefore defined for use in therapy.

In a further aspect, the present invention provides the use of a compound of formula (I), or a pharmaceutically acceptable salt or solvate thereof, or a solvate of such a salt, as hereinbefore defined in the manufacture of a medicament for use in therapy.

In the context of the present invention, the term "therapy" includes "prophylaxis" unless there are specific indications to the contrary. The terms "therapeutic" and "therapeutically" should be understood accordingly.

The invention also provides a method of treating a condition where inhibition of carboxypeptidase U is beneficial in a mammal suffering from, or at risk of, said condition, which comprises administering to the mammal a therapeutically effective amount of a compound of formula (I), or a pharmaceutically acceptable salt or solvate thereof, or a solvate of such a salt, as hereinbefore defined.

For the above-mentioned therapeutic uses the dosage administered will vary with the compound employed, the mode of administration, the treatment desired and the disorder indicated.

The compounds of formula (I) and pharmaceutically acceptable salts, solvates or solvates of salts thereof may be used on their own but will generally be administered in the form of a pharmaceutical composition in which the formula (I) compound, salt, solvate or solvate of salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention thus also provides a pharmaceutical composition comprising a compound of formula (I), or a pharmaceutically acceptable salt or solvate thereof, or a solvate of such a salt, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, or a solvate of such a salt, as hereinbefore defined, with a pharmaceutically acceptable adjuvant, diluent or carrier.

Also included in the invention are derivatives of compounds of formula (I) which have the biological function of compounds of formula (I), such as prodrugs. Prodrugs are, for example, (pivaloyloxy)methyl esters and [(ethoxycarbonyl)oxy]methyl esters of carboxylic acids or phosphinic acids.

The following examples illustrate the invention.

EXAMPLES

General Experimental Procedures

Mass spectra were recorded on a Finnigan MAT TSQ 700 triple quadropole mass spectrometer equipped with an electrospray interface (FAB-MS) and VG Platform II mass spectrometer equipped with an electrospray interface (LC-MS). $^1$H NMR measurements were performed on Varian UNITY plus 400, 500 and 600 spectrometers, operating at $^1$H frequencies of 400, 500 and 600 MHz respectively. Chemical shifts are given in ppm with the solvent as internal standard. Organic extracts were dried using $MgSO_4$ or $Na_2SO_4$ as the drying agent. Chromatography separations were performed using Merck Silica gel 60 (0.063-0.200 mm). HPLC separations were performed on a HIGHCROM KR100-10C8 column. SCX columns were purchased from International Sorbent Technology Limited. For methods D and E (see below) NMR samples were typically prepared in the following manner: 100 μL of a 100 mM solution of the compound in DMSO was mixed with DMSO-D6 in an NMR tube. Solvent suppression was applied to the residual protonated DMSO signal by using the standard presat sequence supplied by Varian Software VNMR6.1C using a low power transmitter pulse during 1.5 seconds.

The compounds named below were named using ACD/name version 4.55/03 July 2000 available from Advanced Chemistry Development Inc., Canada.

Preparation A 2-({6-[(tert-Butoxycarbonyl)amino]pyridin-3-yl}methyl)-3-ethoxy-3-oxopropylphosphinic acid was used as starting material and was synthesized as described below.

Bis(trimethylsilyl)phosphonite was generated as described in WO 01/042252 using N,O-bis-(trimethylsilyl) acetamide (3.0 mL; 12.1 mmol) and ammonium hypophosphite (1.0 g; 12.0 mmol). The resulting reaction mixture was cooled to 0° C. and a solution of ethyl 2-({6-[(tert-butoxycarbonyl)amino]pyridin-3-yl}methyl)acrylate (0.72 g; 2.35 mmol), in methylene chloride (4 mL) was added dropwise. The reaction was stirred overnight at room temperature. Methanol was added at 0° C. followed by water. The reaction mixture was concentrated. The remaining residue was dissolved in water and purified by preparative HPLC (0.1 M $NH_4Ac$ (aq)/$CH_3CN$, 1/0→0/1), concentrated and lyophilized to afford 0.56 g (64%) of 2-({6-[(tert-butoxycarbonyl)amino]pyridin-3-yl}methyl)-3-ethoxy-3-oxopropylphosphinic acid.

$^1$H NMR ($CDCl_3$): δ 8.6-8.9 (br s, 1H), 8.13 (s, 1H), 7.85-7.95 (m, 1H), 7.47-7.55 (m, 1H), 7.06 (d, 1H), 4.05 (q, 2H), 2.83-3.05 (m, 3H), 1.9-2.05 (m, 1H), 1.63-1.8 (m, 1H), 1.52 (s, 9H), 1.14 (t, 3H).

Example 1

Preparation of 3-(6-aminopyridin-3-yl)-2-{[benzyl(hydroxy)phosphoryl]methyl}-propanoic acid.

Step (a): Benzyl[2-({6-[(tert-butoxycarbonyl)amino]pyridin-3-yl}methyl)-3-ethoxy-3-oxopropyl]phosphinic acid Argon was bubbled through a mixture of BSTFA (0.3 mL; 1.3 mmol), benzyl bromide (0.1 mL; 0.7 mmol), and $CH_2Cl_2$ (1.5 mL) for 10 minutes. 2-({6-[(tert-Butoxycarbonyl) amino]pyridin-3-yl}methyl)-3-ethoxy-3-oxopropylphosphinic acid (50 mg; 0.13 mmol) was added, and the reaction mixture was refluxed under argon for 1 h. The solution was concentrated to afford 0.13 g of crude benzyl[2-({6-[(tert-butoxycarbonyl)amino]pyridin-3-yl}methyl)-3-ethoxy-3-oxopropyl]phosphinic acid.

Step (b): 3-[Benzyl(hydroxy)phosphoryl]-2-({6-[(tert-butoxycarbonyl)amino]pyridin-3-yl}methyl)propanoic acid Benzyl[2-({6-[(tert-butoxycarbonyl)amino]pyridin-3-yl}methyl)-3-ethoxy-3-oxopropyl]phosphinic acid (62 mg; 0.13 mmol) was dissolved in THF (1 mL) and water (1 mL). LiOH (12 mg; 0.5 mmol) was added, and the reaction was stirred at room temperature overnight. The reaction mixture was concentrated, water (1 mL) was added and the aqueous solution was extracted with $CHCl_3$ (1×1 mL). 0.5 M aqueous HCl (1 mL) was added to the aqueous solution, and the resulting acidic aqueous solution was extracted with $CHCl_3$ (3×2 mL). The combined organic phases were dried and concentrated to afford 46 mg (81%) of 3-[benzyl(hydroxy)phosphoryl]-2-({6-[(tert-butoxycarbonyl)amino]-pyridin-3-yl}methyl)propanoic acid.

Step (c): 3-(6-Aminopyridin-3-yl)-2-{[benzyl(hydroxy)phosphoryl]methyl}propanoic acid 3-[Benzyl(hydroxy)phosphoryl]-2-({6-[(tert-butoxycarbonyl)amino]pyridin-3-yl}methyl)propanoic acid (46 mg; 0.11 mmol) was dissolved in EtOAc (2 mL) and 1 mL of EtOAc, which had been saturated with HCl (g), was added. The reaction was stirred at room temperature overnight. The reaction mixture was concentrated to yield 25 mg (64%) of 3-(6-aminopyridin-3-yl)-2-{[benzyl(hydroxy)phosphoryl]methyl}propanoic acid.

$^1$H NMR ($D_2O$): δ 7.74 (s, 1H), 7.53-7.6 (m, 1H), 7.2-7.4 (m, 5H), 6.73 (d, 1H), 3.0 (d, 2H), 2.83-2.9 (m, 1H), 2.6-2.78 (m, 2H), 1.83-1.95 (m, 1H), 1.5-1.63 (m, 1H).

Methods A to E describe general methods by which compounds of formula (I) can be prepared.

Method A

The reactions were performed using a Chemspeed automated synthesizer from Chemspeed Ltd., Augst, Switzerland.

A solution of the selected $R^1CH_2$halide (0.65 mmol) in $CH_2Cl_2$ (1.5 mL) was added to a degassed solution of 2-({6-[(tert-butoxycarbonyl)amino]pyridin-3-yl}methyl)-3-ethoxy-3-oxopropylphosphinic acid (0.13 mmol) and BSTFA (1.3 mmol) in $CH_2Cl_2$ (1.5 mL). After reflux for 2 hours under argon atmosphere $CH_2Cl_2$ (1 mL) was added, and the reaction mixture was concentrated. $CH_2Cl_2$ (2 mL) was added, and the product was extracted with 2 M aqueous HCl. The aqueous phase was concentrated. THF (1.5 mL) and 0.43 M aqueous LiOH (1.5 mL) were added, and the reaction mixture was stirred at 30° C. overnight. The reaction mixture was concentrated. The crude product was dissolved in $MeOH/THF/H_2O$ and loaded onto an SCX column (2 g). The SCX column was then washed with $CH_2Cl_2$ (2 mL) followed by THF (2 mL), and this procedure was repeated once more. Finally, the product was eluted using a saturated solution of $NH_3$ in MeOH (2×4 mL). The solution was concentrated to afford the product as its corresponding bis-ammonium salt.

Method B

Microwave heating was used in the reactions with the aid of a Smith synthesiser operating at 2450 MHz from Personalchemistry, Uppsala, Sweden.

A solution of the selected $R^1CH_2$bromide (0.44 mol) in $CH_2Cl_2$ (1 mL) was added to a solution of 2-({6-[(tert-butoxycarbonyl)amino]pyridin-3-yl}methyl)-3-ethoxy-3-oxopropylphosphinic acid (0.09 mmol) and BSTFA (0.9 mmol) in $CH_2Cl_2$ (1 mL). The reaction mixture was stirred for 5 minutes at 140° C. TFA (0.5 mL) was added, and stirring was continued for 5 minutes at 120° C. The reaction mixture was concentrated. $CH_2Cl_2$ (4 mL) was added, and the resulting solution was poured onto an SCX column (2 grams). The SCX column was then washed with $CH_2Cl_2$ (2 mL) followed by THF (2 mL), and this procedure was repeated once more. The carboxylic ester was eluted from the column using a saturated solution of $NH_3$ in MeOH. The solution was concentrated.

THF (1 mL) and 0.43 M aqueous LiOH (1 mL) were added. The reaction mixture was stirred overnight at room temperature. Addition of 2 M aqueous HCl (0.5 mL) followed by evaporation afforded the crude product. Purification was performed using preparative HPLC (0.1 M $NH_4Ac$ (aq)/$CH_3CN$; 95/5→0/1) to afford the product as its corresponding bis-ammonium salt.

Method C

A solution of the selected $R^1CH_2$halide (0.65 mmol) in $CH_2Cl_2$ (1.5 mL) was added to a degassed solution of 2-({6-[(tert-butoxycarbonyl)amino]-pyridin-3-yl}methyl)-3-ethoxy-3-oxopropylphosphinic acid (0.13 mmol) and bis(trimethylsilyl)trifluoroacetamide (BSTFA) (1.3 mmol) in $CH_2Cl_2$ (1.5 mL). After reflux for 2 hours under nitrogen atmosphere using a Chemspeed automated synthesizer $CH_2Cl_2$ (1 mL) was added, and the mixture was concentrated. $CH_2Cl_2$ (4 mL) was added and the mixture was loaded onto an SCX column (2 grams). The SCX column was then washed with $CH_2Cl_2$ (2 mL) followed by THF (2 mL), and this procedure was repeated once more. The carboxylic ester was eluted from the column using a saturated solution of $NH_3$ in MeOH. The solution was concentrated. THF (1.5 mL) and 0.43 M aqueous LiOH (1.5 mL) were added. The reaction mixture was stirred overnight at 30° C. After evaporation 4 M HCl in dioxane (1 mL) was added. The resulting mixture was stirred for 5 hours at room temperature and concentrated. The crude product was purified using preparative HPLC (0.1 M TFA (aq)/$CH_3CN$; 95/5→0/1) to afford the product as its corresponding trifluoroacetate salt.

Method D

Microwave heating was used in the reactions with the aid of a Smith synthesiser operating at 2450 MHz from Personalchemistry, Uppsala, Sweden.

A solution of the selected $R^1CH_2$bromide (0.44 mol) in $CH_2Cl_2$ (1 mL) was added to a solution of 2-({6-[(tert-butoxycarbonyl)amino]pyridin-3-yl}methyl)-3-ethoxy-3-oxopropylphosphinic acid (0.09 mmol) and BSTFA (0.9 mmol) in $CH_2Cl_2$ (1 mL). The reaction mixture was stirred for 5 minutes at 140° C. TFA (0.5 mL) was added, and stirring was continued for 5 minutes at 120° C. The reaction mixture was concentrated. $CH_2Cl_2$ (4 mL) was added, and the resulting solution was poured onto an SCX column (2 grams). The SCX column was then washed with $CH_2Cl_2$ (2 mL) followed by THF (2 mL), and this procedure was repeated once more. The carboxylic ester was eluted from the column using a saturated solution of NH₃ in MeOH. The solution was concentrated.

THF (1 mL) and 0.43 M aqueous LiOH (1 mL) were added. The reaction mixture was stirred overnight at room temperature. Addition of 2 M aqueous HCl (0.5 mL) followed by evaporation afforded the crude product. The crude product was purified using preparative HPLC (0.1 M TFA (aq)/CH₃CN; 95/5→0/1) to afford the product as its corresponding trifluoroacetate salt.

The following compounds are examples of compounds of formula (I):

3-(6-Aminopyridin-3-yl)-2-{[(4-cyanobenzyl)(hydroxy) phosphoryl]methyl}propanoic acid was synthesized according to method A.

M(+) 360 (M+1)

$^1$H NMR (D₂O) δ 7.55-7.8 (m, 4H), 7.35-7.45 (m, 2H), 6.74-6.8 (m, 1H), 3.05 (d, 2H), 2.8-2.9 (m, 1H), 2.6-2.75 (m, 2H), 1.8-1.95 (m, 1H), 1.48-1.64 (m, 1H).

3-(6-Aminopyridin-3-yl)-2-{[hydroxy(2-methoxy-5-nitrobenzyl)phosphoryl]methyl}propanoic acid was synthesized according to method A.

M(+) 410 (M+1)

$^1$H NMR (D₂O) δ 8.13-8.2 (m, 2H), 7.67 (s, 1H), 7.55-7.6 (m, 1H), 7.04-7.1 (m, 1H), 6.74 (d, 1H), 3.93 (s, 3H), 3.0-3.1 (m, 2H), 2.85-2.95 (m, 1H), 2.55-2.75 (m, 2H), 1.82-1.93 (m, 1H), 1.5-1.63 (m, 1H).

3-(6-Aminopyridin-3-yl)-2-{[(2,4-difluorobenzyl)(hydroxy)phosphoryl]methyl}propanoic acid was synthesized according to method A.

M(+) 371 (M+1)

$^1$H NMR (D₂O) δ 7.6-7.75 (m, 2H), 7.25-7.4 (m, 1H), 6.9-7.0 (m, 2H), 6.8 (d, 1H), 2.84-3.04 (m, 3H), 2.56-2.78 (m, 2H), 1.8-1.97 (m, 1H), 1.52-1.68 (m, 1H).

3-(6-Aminopyridin-3-yl)-2-{[[(2,6-dichloropyridin-4-yl) methyl](hydroxy)phosphoryl]-methyl}propanoic acid was synthesized according to method A.

M(+) 405 (M+1)

$^1$H NMR (D₂O) δ 7.7 (br s, 1H), 7.56-7.62 (m, 1H), 7.34 (br s, 2H), 6.74-6.8 (m, 1H), 3.0 (d, 2H), 2.77-2.88 (m, 1H), 2.62-2.76 (m, 2H), 1.85-1.97 (m, 1H), 1.51-1.64 (m, 1H).

3-(6-Aminopyridin-3-yl)-2-{[(2-fluorobenzyl)(hydroxy) phosphoryl]methyl}propanoic acid was synthesized according to method A.

M(+) 353 (M+1)

$^1$H NMR (D₂O) δ 7.6-7.8 (m, 2H), 7.2-7.4 (m, 2H), 7.05-7.2 (m, 2H), 6.8 (d, 1H), 3.0 (d, 2H), 2.86-2.94 (m, 1H), 2.56-2.78 (m, 2H), 1.8-1.97 (m, 1H), 1.53-1.65 (m, 1H).

3-(6-Aminopyridin-3-yl)-2-{[(2-cyanobenzyl)(hydroxy) phosphoryl]methyl}propanoic acid was synthesized according to method A.

M(+) 360 (M+1)

$^1$H NMR (D₂O) δ 7.66-7.76 (m, 2H), 7.56-7.66 (m, 2H), 7.44-7.5 (m, 1H), 7.34-7.44 (m, 1H), 6.77 (d, 1H), 3.2 (d, 2H), 2.8-2.95 (m, 1H), 2.6-2.8 (m, 2H), 1.85-2.0 (m, 1H), 1.55-1.7 (m, 1H).

3-(6-Aminopyridin-3-yl)-2-{[(2-bromobenzyl)(hydroxy) phosphoryl]methyl}propanoic acid was synthesized according to method A.

M(+) 413 and 415 (M+1)

$^1$H NMR (D₂O) δ 7.68 (s, 1H), 7.55-7.65 (m, 2H), 7.36-7.46 (m, 1H), 7.3-7.36 (m, 1H), 7.1-7.2 (m, 1H), 6.77 (d, J=8.8 Hz, 1H), 3.21 (d, 2H), 2.84-2.94 (m, 1H), 2.56-2.76 (m, 2H), 1.85-2.0 (m, 1H), 1.54-1.68 (m, 1H).

3-(6-Aminopyridin-3-yl)-2-{[hydroxy(2-hydroxy-5-nitrobenzyl)phosphoryl]methyl}propanoic acid was synthesized according to method A.

M(+) 396 (M+1)

3-(6-Aminopyridin-3-yl)-2-{[(3-cyanobenzyl)(hydroxy) phosphoryl]methyl}propanoic acid was synthesized according to method A.

M(+) 360 (M+1)

$^1$H NMR (D₂O) δ 7.4-7.7 (m, 6H), 6.82 (d, 1H), 3.0 (d, 2H), 2.8-2.9 (m, 1H), 2.6-2.8 (m, 2H), 1.8-1.95 (m, 1H), 1.48-1.63 (m, 1H).

3-(6-Aminopyridin-3-yl)-2-{[(3-benzoylbenzyl)(hydroxy) phosphoryl]methyl}propanoic acid was synthesized according to method A.

M(+) 439 (M+1)

3-(6-Aminopyridin-3-yl)-2-{[hydroxy(3-methylbenzyl) phosphoryl]methyl}propanoic acid was synthesized according to method A.

M(+) 349 (M+1)

$^1$H NMR (D₂O) δ 7.8 (s, 1H), 7.4-7.55 (m, 1H), 7.2-7.3 (m, 1H), 7.0-7.2 (m, 3H), 6.66 (d, 1H), 2.93 (d, 2H), 2.8-2.9 (m, 1H), 2.58-2.75 (m, 2H), 2.31 (s, 3H), 1.8-1.95 (m, 1H), 1.5-1.65 (m, 1H).

3-(6-Aminopyridin-3-yl)-2-({hydroxy[4-(1,2,3-thiadiazol-4-yl)benzyl]phosphoryl}methyl)propanoic acid was synthesized according to method A.

M(+) 419 (M+1)

$^1$H NMR (D₂O) δ 7.9-8.0 (m, 2H), 7.8 (s, 1H), 7.4-7.5 (m, 4H), 6.61 (d, 1H), 3.05 (d, 2H), 2.75-2.85 (m, 1H), 2.6-2.75 (m, 2H), 1.85-1.95 (m, 1H), 1.53-1.65 (m, 1H).

3-(6-Aminopyridin-3-yl)-2-{[[(1-bromo-2-naphthyl)methyl](hydroxy)phosphoryl]methyl}-propanoic acid was synthesized according to method B.

M(+) 463 and 465 (M+1)

3-(6-Aminopyridin-3-yl)-2-{[(4-chlorobenzyl)(hydroxy) phosphoryl]methyl}propanoic acid was synthesized according to method B.

M(+) 369 (M+1)

$^1$H NMR (D₂O) δ 7.68-7.74 (m, 1H), 7.58-7.66 (m, 1H), 7.3-7.38 (m, 2H), 7.2-7.3 (m, 2H), 6.88 (d, 1H), 2.95 (d, 2H), 2.6-2.7 (m, 3H), 1.75-1.9 (m, 1H), 1.45-1.6 (m, 1H).

3-(6-Aminopyridin-3-yl)-2-{[(1,1'-biphenyl-4-ylmethyl) (hydroxy)phosphoryl]methyl}-propanoic acid was synthesized according to method B.

M(+) 411 (M+1)

3-(6-Aminopyridin-3-yl)-2-{[(3-fluorobenzyl)(hydroxy) phosphoryl]methyl}propanoic acid was synthesized according to method B.

M(+) 353 (M+1)

$^1$H NMR (D₂O) δ 7.58-7.75 (m, 2H), 7.26-7.36 (m, 1H), 6.94-7.1 (m, 3H), 6.86 (d, 1H), 2.98 (d, 2H), 2.83-2.91 (m, 1H), 2.6-2.76 (m, 2H), 1.8-1.95 (m, 1H), 1.5-1.65 (m, 1H).

3-(6-Aminopyridin-3-yl)-2-{[(3-chlorobenzyl)(hydroxy) phosphoryl]methyl}propanoic acid was synthesized according to method B.

M(+) 369 (M+1)

$^1$H NMR (D₂O) δ 7.6-7.7 (m, 2H), 7.15-7.36 (m, 4H), 6.84 (d, 1H), 2.96 (d, 2H), 2.82-2.88 (m, 1H), 2.58-2.74 (m, 2H), 1.8-1.95 (m, 1H), 1.5-1.63 (m, 1H).

3-(6-Aminopyridin-3-yl)-2-{[hydroxy(4-methylbenzyl)phosphoryl]methyl}propanoic acid was synthesized according to method B.
M(+) 349 (M+1)
$^1$H NMR (D$_2$O) δ 7.58-7.68 (m, 2H), 6.96-7.3 (m, 4H), 6.83 (d, 1H), 2.92 (d, 2H), 2.8-2.88 (m, 1H), 2.56-2.74 (m, 2H), 2.30 (s, 3H), 1.75-1.83 (m, 1H), 1.45-1.60 (m, 1H).

3-(6-Aminopyridin-3-yl)-2-{[(3-bromobenzyl)(hydroxy)phosphoryl]methyl}propanoic acid was synthesized according to method B.
M(+) 413 and 415 (M+1)
$^1$H NMR (D$_2$O) δ 7.54-7.66 (m, 2H), 7.36-7.5 (m, 2H), 7.14-7.26 (m, 2H), 6.81 (d, 1H), 2.94 (d, 2H), 2.75-2.85 (m, 1H), 2.6-2.7 (m, 2H), 1.75-1.95 (m, 1H), 1.47-1.6 (m, 1H).

3-(6-Aminopyridin-3-yl)-2-{[hydroxy(2-naphthylmethyl)phosphoryl]methyl}propanoic acid was synthesized according to method B.
M(+) 385 (M+1)

3-(6-Aminopyridin-3-yl)-2-{[hydroxy(2-nitrobenzyl)phosphoryl]methyl}propanoic acid was synthesized according to method B.
M(+) 380 (M+1)
$^1$H NMR (D$_2$O) δ 7.98 (d, 1H), 7.56-7.7 (m, 3H), 7.4-7.5 (m, 2H), 6.82 (d, 1H), 3.39-3.55 (m, 2H), 2.83-2.91 (m, 1H), 2.58-2.75 (m, 2H), 1.83-1.95 (m, 1H), 1.5-1.63 (m, 1H).

3-(6-Aminopyridin-3-yl)-2-{[(4-fluorobenzyl)(hydroxy)phosphoryl]methyl}propanoic acid was synthesized according to method B.
M(+) 353 (M+1)
$^1$H NMR (D$_2$O) δ 7.58-7.7 (m, 2H), 7.18-7.3 (m, 2H), 7.0-7.1 (m, 2H), 6.83 (d, 1H), 2.94 (d, 2H), 2.8-2.9 (m, 1H), 2.6-2.74 (m, 2H), 1.8-1.93 (m, 1H), 1.47-1.63 (m, 1H).

3-(6-Aminopyridin-3-yl)-2-({hydroxy[2-(trifluoromethoxy)benzyl]phosphoryl}methyl)-propanoic acid was synthesized according to method B.
M(+) 419 (M+1)
$^1$H NMR (D$_2$O) δ 7.58-7.7 (m, 2H), 7.4-7.48 (m, 1H), 7.26-7.38 (m, 3H), 6.84 (d, 1H), 3.06 (d, 2H), 2.82-2.9 (m, 1H), 2.6-2.75 (m, 2H), 1.83-1.94 (m, 1H), 1.5-1.63 (m, 1H).

3-(6-Aminopyridin-3-yl)-2-{[(3,5-dimethylbenzyl)(hydroxy)phosphoryl]methyl}propanoic acid was synthesized according to method B.
M(+) 363 (M+1)

3-(6-Aminopyridin-3-yl)-2-({hydroxy[4-(trifluoromethyl)benzyl]phosphoryl}methyl)propanoic acid was synthesized according to method B.
M(+) 403 (M+1)
$^1$H NMR (D$_2$O) δ 7.55-7.7 (m, 4H), 7.35-7.45 (m, 2H), 6.81 (d, 1H), 3.05 (d, 2H), 2.8-2.9 (m, 1H), 2.6-2.75 (m, 2H), 1.8-1.95 (m, 1H), 1.48-1.6 (m, 1H).

3-(6-Aminopyridin-3-yl)-2-{[(1,1'-biphenyl-2-ylmethyl)(hydroxy)phosphoryl]methyl}-propanoic acid was synthesized according to method B.
M(+) 411 (M+1)
$^1$H NMR (D$_2$O) δ 7.25-7.6 (m, 11 H), 6.81 (d, 1H), 3.05 (d, 2H), 2.6-2.8 (m, 1H), 2.4-2.6 (m, 2H), 1.5-1.7 (m, 1H), 1.25-1.4 (m, 1H).

3-(6-Aminopyridin-3-yl)-2-[(hydroxy{4-[(trifluoromethyl)thio]benzyl}phosphoryl)methyl]propanoic acid was synthesized according to method C.
M(+) 435 (M+1)
$^1$H NMR (DMSO-D6) δ 7.6-7.75 (m, 3H), 7.3-7.5 (m, 3H), 6.8 (d, 1H), 3.3 (d, 2H), 2.72-2.85 (m, 3H), 1.84-1.95 (m, 1H), 1.57-1.7 (m, 1H).

3-(6-Aminopyridin-3-yl)-2-{[[(9,10-dioxo-9,10-dihydroanthracen-2-yl)methyl](hydroxy)-phosphoryl]methyl}propanoic acid was synthesized according to method C.
M(+) 465 (M+1)

3-(6-Aminopyridin-3-yl)-2-[(hydroxy{2-[(trifluoromethyl)thio]benzyl}phosphoryl)methyl]propanoic acid was synthesized according to method C.
M(+) 435 (M+1)
$^1$H NMR (DMSO-D6) δ 7.72-7.85 (br s, 1H), 7.65-7.72 (m, 2H), 7.55-7.65 (m, 2H), 7.3-7.4 (m, 2H), 6.85 (d, 1H), 3.1 (d, 2H), 2.7-2.86 (m, 3H), 1.82-1.95 (m, 1H), 1.53-1.65 (m, 1H).

3-(6-Aminopyridin-3-yl)-2-({hydroxy[4-methylsulfonyl)benzyl]phosphoryl}methyl)propanoic acid was synthesized according to method C.
M(+) 413 (M+1)
$^1$H NMR (DMSO-D6) δ 7.9-8.05 (br s, 1H), 7.7-7.85 (m, 4H), 7.45-7.52 (m, 2H), 6.91 (d, 1H), 3.21 (d, 2H), 3.17 (s) (3H), 2.71-2.87 (m, 3H), 1.87-2.0 (m, 1H), 1.56-1.7 (m) (1H).

3-(6-Aminopyridin-3-yl)-2-{[[(2'-cyano-1,1'-biphenyl-4-yl)methyl](hydroxy)phosphoryl]-methyl}propanoic acid was synthesized according to method C.
M(+) 436 (M+1)
$^1$H NMR (DMSO-D6) δ 7.87-8.0 (m, 2H), 7.7-7.8 (m, 3H), 7.52-7.62 (m, 2H), 7.45-7.52 (m, 2H), 7.34-7.4 (m, 2H), 6.91 (d, 1H), 3.15 (d, 2H), 2.7-2.9 (m, 3H), 1.9-2.03 (m, 1H), 1.6-1.7 (m, 1H).

3-(6-Aminopyridin-3-yl)-2-({hydroxy[4-({[2-(1H-indol-3-yl)ethyl]amino}sulfonyl)benzyl]phosphoryl}methyl)propanoic acid was synthesized according to method C.
M(+) 557 (M+1)

3-(6-Aminopyridin-3-yl)-2-{[[4-({[2-(3,4-dimethoxyphenyl)ethyl]amino}sulfonyl)benzyl](hydroxy)phosphoryl]methyl}propanoic acid was synthesized according to method C.
M(+) 578 (M+1)

3-(6-Aminopyridin-3-yl)-2-{[[3-(2-fluorophenoxy)benzyl](hydroxy)phosphoryl]methyl}-propanoic acid was synthesized according to method C.
M(+) 445 (M+1)
$^1$H NMR (DMSO-D6) δ 7.5-7.7 (m, 2H), 7.3-7.4 (m, 1H), 7.14-7.28 (m, 3H), 7.06-7.14 (m, 1H), 6.85-7.0 (m, 2H), 6.7-6.85 (m, 2H), 3.03 (d, 2H), 2.7-2.83 (m, 3H), 1.8-1.9 (m, 1H), 1.5-1.6 (m, 1H).

3-(6-Aminopyridin-3-yl)-2-{[hydroxy(4-iodobenzyl)phosphoryl]methyl}propanoic acid was synthesized according to method C.
M(+) 461 (M+1)
$^1$H NMR (DMSO-D6) δ 7.85-8.0 (br s, 1H), 7.68-7.78 (m, 2H), 7.58-7.65 (m, 2H), 7.0-7.06 (m, 2H), 6.90 (d, 1H), 3.0 (d, 2H), 2.7-2.86 (m, 3H), 1.82-1.94 (m, 1H), 1.5-1.63 (m, 1H).

3-(6-Aminopyridin-3-yl)-2-{[[(5-chloro-1-benzothien-3-yl)methyl](hydroxy)phosphoryl]-methyl}propanoic acid was synthesized according to method C.
M(+) 425 (M+1)

¹H NMR (D₂O) δ 7.96-8.04 (m, 2H), 7.86-7.96 (br s, 1H), 7.66-7.76 (m, 2H), 7.56-7.6 (m, 1H), 7.34-7.4 (m, 1H), 6.87 (d, 1H), 3.36 (d, 2H), 2.7-2.9 (m, 3H), 1.93-2.05 (m, 1H), 1.62-1.75 (m, 1H).

3-(6-Aminopyridin-3-yl)-2-{[(3,5-dibromo-2-hydroxybenzyl)(hydroxy)phosphoryl]methyl}propanoic acid was synthesized according to method C.
M(+) 507, 509 and 511 (M+1)

3-(6-Aminopyridin-3-yl)-2-{[{[4-chloro-2-(trifluoromethyl)quinolin-6-yl]methyl}(hydroxy)phosphoryl]methyl}propanoic acid was synthesized according to method C.
M(+) 488 (M+1)

3-(6-Aminopyridin-3-yl)-2-{[(4,5-dimethoxy-2-nitrobenzyl)(hydroxy)phosphoryl]methyl}-propanoic acid was synthesized according to method C.
M(+) 440 (M+1)

3-(6-Aminopyridin-3-yl)-2-{[[3-(4-fluorophenoxy)benzyl](hydroxy)phosphoryl]methyl}-propanoic acid was synthesized according to method D.
M(+) 445 (M+1)

3-(6-Aminopyridin-3-yl)-2-{[[2-fluoro-5-(trifluoromethyl)benzyl](hydroxy)phosphoryl]-methyl}propanoic acid was synthesized according to method D.
M(+) 421 (M+1)
¹H NMR (DMSO-D6) δ 7.8-8.0 (br s, 1H), 7.6-7.8 (m, 4H), 7.3-7.4 (m, 1H), 6.9 (d, 1H), 3.19 (d, 2H), 2.7-2.9 (m, 3H), 1.93-2.05 (m, 1H), 1.63-1.8 (m, 1H).

3-(6-Aminopyridin-3-yl)-2-{[[2-fluoro-3-(trifluoromethyl)benzyl](hydroxy)phosphoryl]-methyl}propanoic acid was synthesized according to method D.
M(+) 421 (M+1)
¹H NMR (DMSO-D6) δ 7.8-8.0 (br s, 1H), 7.6-7.8 (m, 4H), 7.3-7.4 (m, 1H), 6.9 (d, 1H), 3.18 (d, 2H), 2.7-2.9 (m, 3H), 1.9-2.05 (m, 1H), 1.63-1.8 (m, 1H).

3-(6-Aminopyridin-3-yl)-2-{[[3-fluoro-5-(trifluoromethyl)benzyl](hydroxy)phosphoryl]-methyl}propanoic acid was synthesized according to method D.
M(+) 421 (M+1)
¹H NMR (DMSO-D6) δ 7.8-8.0 (br s, 1H), 7.7-7.8 (m, 2H), 7.35-7.55 (m, 3H), 6.9 (d, 1H), 3.23 (d, 2H), 2.7-2.9 (m, 3H), 1.87-2.0 (m, 1H), 1.56-1.68 (m, 1H).

3-(6-Aminopyridin-3-yl)-2-{[[2-fluoro-6-(trifluoromethyl)benzyl](hydroxy)phosphoryl]-methyl}propanoic acid was synthesized according to method D.
M(+) 421 (M+1)

3-(6-Aminopyridin-3-yl)-2-{[[4-fluoro-3-(trifluoromethyl)benzyl](hydroxy)phosphoryl]-methyl}propanoic acid was synthesized according to method D.
M(+) 421 (M+1)
¹H NMR (DMSO-D6) δ 7.8-7.95 (br s, 1H), 7.68-7.77 (m, 2H), 7.6-7.66 (m, 1H), 7.53-7.6 (m, 1H), 7.38-7.45 (m, 1H), 6.88 (d, 1H), 3.17 (d, 2H), 2.7-2.85 (m, 3H), 1.86-1.98 (m, 1H), 1.54-1.67 (m, 1H).

3-(6-Aminopyridin-3-yl)-2-({hydroxy[3-(trifluoromethoxy)benzyl]phosphoryl}methyl)-propanoic acid was synthesized according to method D.
M(+) 419 (M+1)
¹H NMR (DMSO-D6) δ 7.8-8.0 (br s, 1H), 7.65-7.8 (m, 2H), 7.35-7.45 (m, 1H), 7.15-7.3 (m, 3H), 6.9 (d, 1H), 3.14 (d, 2H), 2.7-2.9 (m, 3H), 1.85-1.97 (m, 1H), 1.53-1.65 (m, 1H).

3-(6-Aminopyridin-3-yl)-2-{[[3-fluoro-4-(trifluoromethyl)benzyl](hydroxy)phosphoryl]-methyl}propanoic acid was synthesized according to method D.
M(+) 421 (M+1)
¹H NMR (DMSO-D6) δ 7.8-8.0 (br s, 1H), 7.6-7.8 (m, 3H), 7.2-7.4 (m, 2H), 6.9 (d, 1H), 3.21 (d, 2H), 2.7-2.9 (m, 3H), 1.87-2.0 (m, 1H), 1.55-1.7 (m, 1H).

3-(6-Aminopyridin-3-yl)-2-{[[3-(difluoromethoxy)benzyl](hydroxy)phosphoryl]methyl}-propanoic acid was synthesized according to method D.
M(+) 401 (M+1)
¹H NMR (DMSO-D6) δ 7.8-8.0 (br s, 1H), 7.65-7.8 (m, 2H), 7.3-7.4 (m, 1H), 7.15 (s, 1H), 6.95-7.1 (m, 3H), 6.9 (d, 1H), 3.09 (d, 2H), 2.7-2.9 (m, 3H), 1.85-1.97 (m, 1H), 1.53-1.65 (m, 1H).

3-(6-Aminopyridin-3-yl)-2-({hydroxy[3-(trifluoromethyl)benzyl]phosphoryl}methyl)-propanoic acid was synthesized according to method D.
M(+) 403 (M+1)

3-(6-Aminopyridin-3-yl)-2-{[[2-fluoro-4-(trifluoromethyl)benzyl](hydroxy)phosphoryl]-methyl}propanoic acid was synthesized according to method D.
M(+) 421 (M+1)
¹H NMR (DMSO-D6) 7.8-8.0 (br s, 1H), 7.7-7.8 (m, 2H), 7.45-7.65 (m, 3H), 6.9 (d, 1H), 3.18 (d, 2H), 2.7-2.9 (m, 3H), 1.9-2.05 (m, 1H), 1.63-1.79 (m, 1H).

3-(6-Aminopyridin-3-yl)-2-({hydroxy[2-(trifluoromethyl)benzyl]phosphoryl}methyl)propanoic acid was synthesized according to method D.
M(+) 403 (M+1)
¹H NMR (DMSO-D6) δ 7.8-8.0 (br s, 1H), 7.5-7.8 (m, 5H), 7.35-7.5 (m, 1H), 6.9 (d, 1H), 3.22 (d, 2H), 2.7-2.9 (m, 3H), 1.88-2.0 (m, 1H), 1.57-1.7 (m, 1H).

Abbreviations
AC=acetate
aq=aqueous
BSTFA=bis(trimethylsilyl)-trifluoroacetamide
HPLC=high performance liquid chromatography
TFA=trifluoroacetic acid
THF=tetrahydrofuran

The invention claimed is:
1. A compound of formula (I):

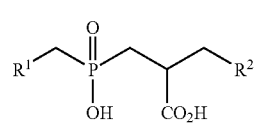

wherein
R¹ is phenyl optionally substituted by halogen, nitro, cyano, hydroxy or $C_{1-6}$ alkyl, which $C_{1-6}$ alkyl is itself optionally substituted by halogen, hydroxy or $S(O)_2R^3$; or
R¹ is phenyl optionally substituted by $C_{1-6}$ alkoxy, which $C_{1-6}$ alkoxy is itself optionally substituted by halogen; or
R¹ is phenyl optionally substituted by $C_{1-6}$ alkylthio, which $C_{1-6}$ alkylthio is itself optionally substituted by halogen; or
R¹ is phenyl optionally substituted by phenyl, phenylcarbonyl, phenyloxy, $S(O)_2R^4$ or $S(O)_2NHR^5$, wherein the phenyl, phenylcarbonyl and phenyloxy rings are optionally substituted by halogen, hydroxy, $C_{1-6}$ alkyl or $C_{1-6}$ alkoxy, wherein the $C_{1-6}$ alkyl or $C_{1-6}$ alkoxy are optionally substituted by halogen; or $R^1$ is 9,10-dihydroanthracenyl optionally substituted by oxo; or $R^1$ is naphthyl optionally substituted by halogen, $C_{1-6}$ alkyl or $C_{1-6}$ alkoxy, wherein the $C_{1-6}$ alkyl or $C_{1-6}$ alkoxy are optionally substituted by halogen;

$R^2$ is aminopyridinyl;

$R^3$ is $C_{1-6}$ alkyl or phenyl;

$R^4$ is $C_{1-6}$ alkyl;

$R^5$ is $(CH_2)_2R^6$; and $R^6$ is phenyl optionally substituted by halogen, $C_{1-6}$ alkyl or $C_{1-6}$ alkoxy, wherein the $C_{1-6}$ alkyl or the $C_{1-6}$ alkoxy are optionally substituted by halogen;

or a pharmaceutically acceptable salt or solvate thereof, or a solvate of such a salt.

2. A compound of claim 1, wherein $R^1$ is phenyl optionally substituted by halogen, nitro, cyano, hydroxy or $C_{1-6}$ alkyl, which $C_{1-6}$ alkyl is itself optionally substituted by halogen, hydroxy or $S(O)_2R^3$; or $R^1$ is $C_{1-6}$ alkoxy optionally substituted by halogen; or $R^1$ is $C_{1-6}$ alkylthio optionally substituted by halogen; or $R^1$ is phenyl optionally substituted by phenyl, phenylcarbonyl, phenyloxy, $S(O)_2R^4$, or $S(O)_2NHR^5$, wherein the phenyl, phenylcarbonyl and phenyloxy rings are optionally substituted by halogen, hydroxy, $C_{1-6}$ alkyl or $C_{1-6}$ alkoxy, wherein the $C_{1-6}$ alkyl and $C_{1-6}$ alkoxy are optionally subsituted by halogen;

$R^3$ is $C_{1-6}$ alkyl or phenyl; p1 $R^4$ is $C_{1-6}$ alkyl;

$R^5$ is $(CH_2)_2R^6$; and $R^6$ is phenyl optionally substituted by halogen, $C_{1-6}$ alkyl or $C_{1-6}$ alkoxy, wherein the $C_{1-6}$ alkyl and $C_{1-6}$ alkoxy are optionally substituted by halogen.

3. A compound of claim 1, wherein $R^1$ is phenyl optionally substituted by halogen, nitro, cyano, $CF_3$ or $OCF_3$.

4. A compound of claim 1, wherein $R^2$ is 6-aminopyridin-3-yl.

5. A pharmaceutical composition comprising a compound according to any one of claims 1 to 4 as active ingredient in combination with a pharmaceutically acceptable adjuvant, diluent or carrier.

* * * * *